(12) United States Patent
Xiao et al.

(10) Patent No.: US 11,357,710 B2
(45) Date of Patent: Jun. 14, 2022

(54) SOLID MASK AND PREPARATION METHOD THEREFOR

(71) Applicant: INFINITUS (CHINA) COMPANY LTD., Guangdong (CN)

(72) Inventors: Junyong Xiao, Guangdong (CN); Meiling Tai, Guangdong (CN); Tingshen Zhang, Guangdong (CN); Xiquan Yin, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 170 days.

(21) Appl. No.: 16/843,885

(22) Filed: Apr. 9, 2020

(65) Prior Publication Data

US 2021/0177708 A1 Jun. 17, 2021

(30) Foreign Application Priority Data

Dec. 11, 2019 (CN) .......................... 201911263847.8

(51) Int. Cl.
*A61K 8/02* (2006.01)
*A45D 44/00* (2006.01)
*A61K 8/65* (2006.01)
*A61K 8/73* (2006.01)
*A61Q 19/08* (2006.01)
*D01D 5/00* (2006.01)
*A61K 8/34* (2006.01)
*A61K 8/49* (2006.01)
*A61K 8/55* (2006.01)

(52) U.S. Cl.
CPC .......... *A61K 8/0212* (2013.01); *A45D 44/002* (2013.01); *A61K 8/345* (2013.01); *A61K 8/4926* (2013.01); *A61K 8/4946* (2013.01); *A61K 8/553* (2013.01); *A61K 8/65* (2013.01); *A61K 8/73* (2013.01); *A61K 8/735* (2013.01); *A61Q 19/08* (2013.01); *D01D 5/003* (2013.01)

(58) Field of Classification Search
None
See application file for complete search history.

(56) References Cited

U.S. PATENT DOCUMENTS

2014/0352031 A1* 12/2014 Choi .................... A45D 44/002
2/173

FOREIGN PATENT DOCUMENTS

CN 108135785 6/2018

* cited by examiner

*Primary Examiner* — Melissa S Mercier
(74) *Attorney, Agent, or Firm* — JCIP Global Inc.

(57) ABSTRACT

The present invention provides a solid mask and a preparation method thereof. The solid mask includes a hydrophobic substrate layer and a nanofiber layer, the nanofiber layer has a three-dimensional structure and is electro-spun onto the hydrophobic substrate layer through uniaxial electrostatic spinning technology, and the nanofiber layer is prepared by the following food-grade raw materials in parts by mass: 10 to 30 parts of gelatin, 1 to 30 parts of soya bean lecithin and 0.1 to 10 parts of a functional substance. The present invention provides a solid mask, using gelatin and soya bean lecithin as the framework. The nanofiber layer is a three-dimensional laminate made of fibers having a diameter of a few hundred nanometers. The nanofiber layer has a membrane structure similar to the extracellular matrix. The raw materials of the solid mask are all food-grade raw materials or natural extracts.

16 Claims, 2 Drawing Sheets

SOLID MASK AND PREPARATION METHOD THEREFOR

CROSS-REFERENCE TO RELATED APPLICATION

This application claims the priority benefit of China application serial no. 201911263847.8, filed on Dec. 11, 2019. The entirety of the above-mentioned patent application is hereby incorporated by reference herein and made a part of this specification.

TECHNICAL FIELD

The present invention relates to the technical field of skin care products, and specifically relates to a solid mask and a preparation method therefor.

BACKGROUND

The current mask products are in a form of applying the essence serum on a woven fabric or non-woven fabric, and amount of the essence serum in such kind of product is generally excessive. When in use, the essence serum falls everywhere due to its weight which brings severe inconvenience to the users, and relatively long life-time is required. Essence ingredients of the mask, such as vitamins, enzymes, proteins, peptides and etc., are preserved for long term use in a liquid form, and stabilizers and preservatives are needed which affect the usage safety. In addition, the additive amount of a part of the essence ingredients is relatively low due to its high price, and the essence ingredients cannot be dispersed uniformly during the impregnation of substrate materials such as non-woven fabrics, and because fully impregnation of non-woven fabric is required, excessive essence serum is added. However, because some substrates such as non-woven fabrics, etc. absorb part of the essence serum, and part of the essence serum is stuck in the packaging bag and cannot be fully squeezed out, some of the essence serum is lost, resulting in a large amount of essence serum is wasted and cannot be completely used on the face and absorbed by the skin. If expensive essence ingredients with low utilization rate are added excessively, wherein the essence serum cannot be completely absorbed, thus resulting in low utilization rate of expensive essence ingredients, which increases production costs.

In order to solve the above-mentioned problems, solid masks, especially solid masks prepared by electrostatic spinning technology, have emerged. The solid mask has the following two advantages: 1) the essence serum is integrated with the substrate cloth, which improves the stability of functional substances, reduces the content of additives, and is easy to preserve and carry; 2) when used, only a small amount of water or essence serum is needed to moisten the solid mask, and there is no essence serum flowing phenomenon, which is convenient and quick. However, due to the characteristics of electrostatic spinning, artificially synthesized polymer materials are added during the preparation of many solid masks to assist the electrospinning. For example, polyethylene glycol with a high degree of polymerization and a low degree of polymerization is added to the electrospinning solution. CN108135785A discloses a cosmetic mask paper, by adding some water-soluble polymers, such as polyvinyl alcohol, polyvinylpyrrolidone, polyethylene oxide, carboxymethyl cellulose, polyacrylic acid, etc. and some water-insoluble polymers, such as polyvinylidene fluoride, poly(vinylidene fluoride-co-hexafluoropropylene), perfluoropolymer, polyvinyl chloride, polyvinylidene chloride or their copolymers, polyethylene glycol derivatives, polyoxides, polyacrylonitrile copolymers, polymethyl methacrylate, polymethyl methacrylate copolymer or a mixture thereof, and a functional substance, to form a film layer. These polymer compounds or surfactants are likely to irritate the skin, cause skin irritation, and have poor biocompatibility. In the process of preparing the solid masks, as for some of the solid masks prepared by electrostatic spinning technology, nanofibers formed are prone to agglomeration, knot formation, fractured yarns, holes, etc., which have seriously affected the structure of the nanofibers, resulting in a low transdermal absorption rate and reducing the care performance of the mask.

SUMMARY

The technical problems to be solved by the present invention is to overcome the deficiencies and drawbacks of poor biocompatibility and low transdermal absorption rate existing in the solid marks of the prior art, and to provide a solid mask.

The objective of the present invention is to provide a preparation method for the solid mask.

The above objectives of the present invention are realized by the following technical solutions:

A solid mask, which includes a hydrophobic substrate layer and a nanofiber layer, the nanofiber layer has a three-dimensional structure and is electro-spun onto the hydrophobic substrate layer through uniaxial electrostatic spinning technology, and the nanofiber layer is prepared by the following food-grade raw materials in parts by mass: 10 to 30 parts of gelatin, 1 to 30 parts of soya bean lecithin and 0.1 to 10 parts of a functional substance.

Preferably, the nanofiber layer is prepared by the following food-grade raw materials in parts by mass: 18 to 26 parts of gelatin, 2 to 15 parts of soya bean lecithin and 0.2 to 7.5 parts of the functional substance.

More preferably, the nanofiber layer is prepared by the following food-grade raw materials in parts by mass: 24 parts of gelatin, 5 parts of soya bean lecithin and 7.2 parts of the functional substance.

According to the differences between the spinning nozzles, the electrostatic spinning technology has the following kinds including uniaxial, coaxial and triaxial, and etc. The nanofiber layer of the present invention is spun onto the hydrophobic substrate layer through the uniaxial electrostatic spinning technology which is the simplest and convenient for industrialization, while other structures are relatively complicated which brings difficulties for enlargement.

Gelatin and soya bean lecithin are used as the framework in the solid mask of the present invention, wherein gelatin forms a framework for the nanofiber, and also possesses a skin-care activity. Gelatin has a certain moisturizing function, and the gelatin molecules have an excellent compatibility with human skin which is easy to be absorbed by skin and filled between skin matrix layers so as to plump skin, stretch wrinkles and enhance skin elasticity, i.e., having an anti-wrinkling function. Cell membrane is composed of lecithin, and soya bean lecithin can supplement the skin with lecithin, repair the damaged cell membrane and improve the functions of cell membrane, thereby allowing the cell membrane to be softened and rejuvenated, enhancing cell activity and prolonging aging. Meanwhile, the nanofiber membrane has a nanoscale diameter and an extremely high specific surface area of up to 10 $m^2/g$ to 100 $m^2/g$. For its fast dissolution in water, lecithin can self-assemble into nanoparticles and liposomes which are conducive to transdermal absorption of other functional substances.

The hydrophobic substrate layer of the present invention may be selected from a group consisting of non-woven fabrics which is non-absorbent or less-absorbent, iridescent paper, silicone oil paper, and etc.

Compared to the solid mask in the prior art, the solid mask of the present invention possesses the following advantages:

First, the raw materials used by the present invention are all food-grade raw materials or natural extracts, without any high-molecular compounds or surfactants; and the entire solid mask is made of nutrients without other additives or preservatives, having good biocompatibility.

Second, the nanofiber layer in the mask of the present invention is a three-dimensional laminate made of fibers having a diameter of a few hundred nanometers (approximately 200 nm) via the electrostatic spinning technology. Having relatively high specific surface area, the nanofiber layer can enhance loading capacity and solubility of the functional substances, especially insoluble herbal medicine, and can carry various whitening, moisturizing and anti-aging ingredients, so as to be made into various functional masks.

Third, extracellular matrices are macromolecular substances which are secreted to the matrix outside the cell. Collagen, elastin, proteoglycan, glycoprotein and etc. constitute a complex three-dimensional network structure. The electrospinning mask has relatively high specific surface area and the nanofiber membrane has a similar structure to the extracellular matrix, and thus it goes deep within the texture of skin to release the functional substances to the bottom of pore, tending to penetrate the stratum corneum and reach to the deep of the skin, and exerting the effects of moisturizing, whitening and prolonging aging. In addition, after absorbing water, the nanofibers of soya bean lecithin can rapidly assemble into nanoparticles and liposomes which are conducive to transdermal absorption of the other nutrients.

A specific usage of the solid mask of the present invention is as follows:

The mask of the present invention is a solid mask which is easy to preserve the functional substances and convenient to be carried. It is convenient and quick when in use. The mask can be directly applied to the wet face after cleaning the skin without wiping dry, or the solid mask can be applied after moisturizing the skin with pure water or products such as mist spray. In a few seconds, the nano mask is dissolved completely, attached to the skin and exert certain effects. After use, basic skin care or make up can be directly carried out without cleaning. It only needs tens of seconds daily to supplement the skin with the required collagen and make the skin full of energy. Meanwhile, free radicals on the skin surface are removed and the cell membrane is repaired, to provide protection for the skin and defense air pollution, ultraviolet irradiation and computer and mobile phone radiation all day long.

Particularly, the functional substance that may be added to the nanofiber layer of the solid mask of the present invention includes various allowable functional substances, and preferably, the functional substance includes one or more of white tremella polysaccharide, *Saussurea* polysaccharide, *Dendrobium officinale* Kimura et Migo, sodium hyaluronate, glycerin, nicotinamide, collagen, collagen tripeptide and carnosine.

Preferably, the functional substance is a mixture of hydrolyzed collagen, collagen peptide powder, collagen tripeptide and carnosine, wherein a mass ratio of hydrolyzed collagen to collagen peptide powder to collagen tripeptide to carnosine is 1:5:1:0.2.

Preferably, the collagen is collagen peptide powder having an average molecular weight of 2000 Dalton, and the collagen tripeptide has an average molecular weight of 280 Dalton.

Particularly, when the collagen is preferably the collagen peptide powder having an average molecular weight of 2000 Dalton and the collagen tripeptide is preferably small molecules of 280 Dalton, they can effectively penetrate into the stratum corneum and the dermis, and can be directly absorbed by the skin without degradation. Having very strong anti-oxidation, carnosine can clear the reactive oxide species (ROS) and α-β unsaturated aldehyde generated by the over oxidation of aliphatic acid in the cell membrane during the oxidative stress, so as to prevent the skin from aging and exert a whitening effect.

Particularly, the nanofiber layer of the three-dimensional structure constructed by the present invention has a preferable fiber diameter ranging from 80 nm to 800 nm, a thickness of 0.05 mm to 2 mm, and a specific surface area of 10 $m^2/g$ to 100 $m^2/g$. The solid mask prepared by the present invention is an instant-dissolved mask, wherein the dissolution rate is related to the thickness of the nanofiber layer.

The present invention also protects a preparation method for the above-mentioned solid mask, including the following steps:

step 1, preparation of electrospinning solution: adding gelatin, soya bean lecithin and the functional substance to a solvent, followed by mixing to form an even electrospinning solution;

step 2, electrostatic spinning: spinning the electrospinning solution onto the hydrophobic substrate layer by an electrostatic spinning device to prepare and obtain the solid mask, with a working voltage of 10 kV to 28 kV, a feeding velocity of 0.1 mL/hr to 2 mL/hr, a spinning distance of 6 cm to 25 cm, and a relative humidity of working environment of 30% to 50%.

The solvent for the gelatin, the soya bean lecithin and the functional substance may be hexafluoroisopropanol, glycerin or 50-90% acetic acid solution. Particularly, components of the nanofiber layer in step 1 of the present invention are preferably dissolved in the 50-90% acetic acid solution to form an electrospinning solution. Acetic acid is a relatively safe solvent which can dissolve substances that are all screened out and which can be used for electrospinning. Uniform nanofibers cannot be formed if concentration of the acetic acid is too low or too high.

During the electrostatic spinning in step 2, working voltage, feeding velocity and spinning distance are the key parameters of the electrostatic spinning and to which the evenness and diameter of the nanofibers formed are related. The higher the working voltage, the finer the nanofibers; and the nanofibers become thick with the feeding velocity increasing. The spinning distance is related to a receiving area, wherein the shorter the spinning distance the smaller the receiving area. Since the solid mask prepared by the present invention is instant-dissolved, it is sensitive to humidity. When the humidity is too high, the solid mask would get moist; and while the humidity is too low, repulsive force during the electrostatic spinning is relatively strong resulting in uneven spinning.

Preferably, a volume fraction of the acetic acid solution in step 1 is 70%.

Preferably, the working voltage for the electrostatic spinning in step 2 is 15 kV to 23 kV, the feeding velocity is 0.4 mL/hr to 1 mL/hr, the spinning distance is 10 cm to 18 cm, and the relative humidity of working environment is 35% to 45%.

Preferably, the working voltage for the electrostatic spinning in step 2 is 15 kV to 20 kV, the feeding velocity is 0.4 mL/hr to 0.6 mL/hr, the spinning distance is 10 cm to 15 cm, and the relative humidity of working environment is 35% to 40%.

More preferably, the working voltage for the electrostatic spinning in step 2 is 18 kV, the feeding velocity is 0.5 mL/hr, the spinning distance is 12 cm, and the relative humidity of working environment is 35% to 40%.

In order to increase the amount of electrostatic spinning, enhance the productivity and adapt to the industrial production better, the device for electrostatic spinning of the present invention is preferably a multi-head uniaxial electrostatic spinning device or a rolling needle-free electrostatic spinning device.

Compared with the prior art, the present invention has the following beneficial effects:

(1) The present invention provides a solid mask, wherein gelatin and soya bean lecithin are used as the framework which not only provides support but also has a certain activity for skin care and optimizes the transdermal absorption of functional substances, and a total cumulative penetration amount of protein accounts for 130%-160% of that in the raw material group, indicating a good transdermal absorption effect. A total cumulative penetration amount of protein through rat skin can reach up to approximately 1.8 mg, and a retention amount of the protein is only around 0.6 mg.

(2) The nanofiber layer of the solid mask of the present invention is a three-dimensional laminate made of fibers having a diameter of 200 nm. The nanofiber layer has a membrane structure similar to the extracellular matrix, and it can enhance the loading capacity and solubility of the functional substance. Through morphology determination, the nanofiber layer has an extremely high specific surface area which can absorb water quickly and become invisible. Uniform and smooth fibers are formed, without any functional substances leaking out from the fiber layer surface.

(3) The raw materials of the solid mask of the present invention are all food-grade raw materials or natural extracts. It can be verified by a cellular affinity test that the solid mask can accelerate the growth of cell, and by the hen's egg test on the chorioallantoic membrane (HET-CAM) that the mask is nonirritant with good biocompatibility and cellular affinity.

(4) It is verified by an anti-oxidation test that the electro-spinning invisible mask which contains carnosine has skin care activity, repair the damaged cell membrane and has anti-oxidation performance.

Figure 4:
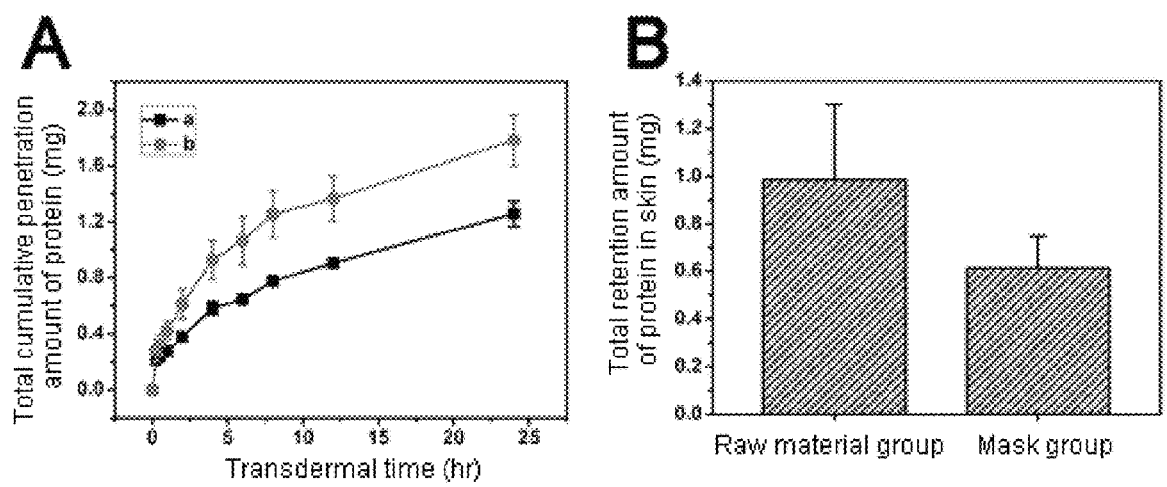

A of FIG. 4 shows curves of total cumulative penetration amounts of protein of a raw material solution (a) and the solid mask S1 (b) varying with transdermal time; B of FIG. 4 shows retention amounts of protein of the raw material solution and the solid mask S1, in rat skin.

DETAILED DESCRIPTION

The present invention is further described hereinafter with reference to the specific examples, but the examples are not intended to limit the invention in any form. Unless defined otherwise, the raw material reagents used in the examples of the invention are conventionally purchased raw material reagents.

Example 1

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 24 parts of gelatin, 5 parts of soya bean lecithin and 7.2 parts of functional substance shown in Table 1.

TABLE 1

| Functional components of different electrospinning solutions | |
|---|---|
| number | Functional components |
| S1 | 1% hydrolyzed collagen, 5% collagen peptide powder (2000 Dalton), 1% collagen tripeptide (molecular weight: 280 Dalton), 0.2% carnosine |
| S2 | — |
| S3 | 1% hydrolyzed collagen |
| S4 | 5% collagen peptide powder (molecular weight: 2000 Dalton) |
| S5 | 5% collagen tripeptide (molecular weight: 280 Dalton) |
| S6 | 5% carnosine |
| S7 | 1% white tremella polysaccharide |
| S8 | 1% *Saussurea* polysaccharide |
| S9 | 1% extract of *Dendrobium officinale* Kimura et Migo |
| S10 | 1% sodium hyaluronate |
| S11 | 1% nicotinamide |
| S12 | 1% glycerin |

A preparation method includes the following steps:

step 1, preparation of electrospinning solution: using 70% (volume fraction) acetic acid solution as a solvent, adding gelatin, soya bean lecithin and a functional substance to the solvent, followed by mixing to form an even electrospinning solution;

step 2, electrostatic spinning: fixing the non-woven substrate layer to the roller, spinning the electrospinning solution of each group onto the hydrophobic substrate layer by an electrostatic spinning device to prepare and obtain solid masks, with a working voltage of 18 kV, a feeding velocity of 0.5 mL/hr, a spinning distance of 12 cm, and a relative humidity of working environment of 35% to 40%.

After a period of electrostatic spinning, the spun hydrophobic substrate layer was removed from the roller and cut by a mask cutter, and then the mask was folded into a quarter size and sealed in an aluminum foil packing bag for later use.

The nanofiber layer prepared had a fiber diameter ranging from 80 nm to 800 nm, approximately 200 nm in average, and a fiber layer thickness of 0.05 mm to 2 mm, 0.5 mm in majority.

Performance Determination:

The results proves that various functional substances of whitening, moisturizing and anti-aging can be all loaded to the instant-dissolved mask which used gelatin and soy bean lecithin as a framework, to prepare the solid masks with various effects.

(1) Morphology Determination

Figure 1:
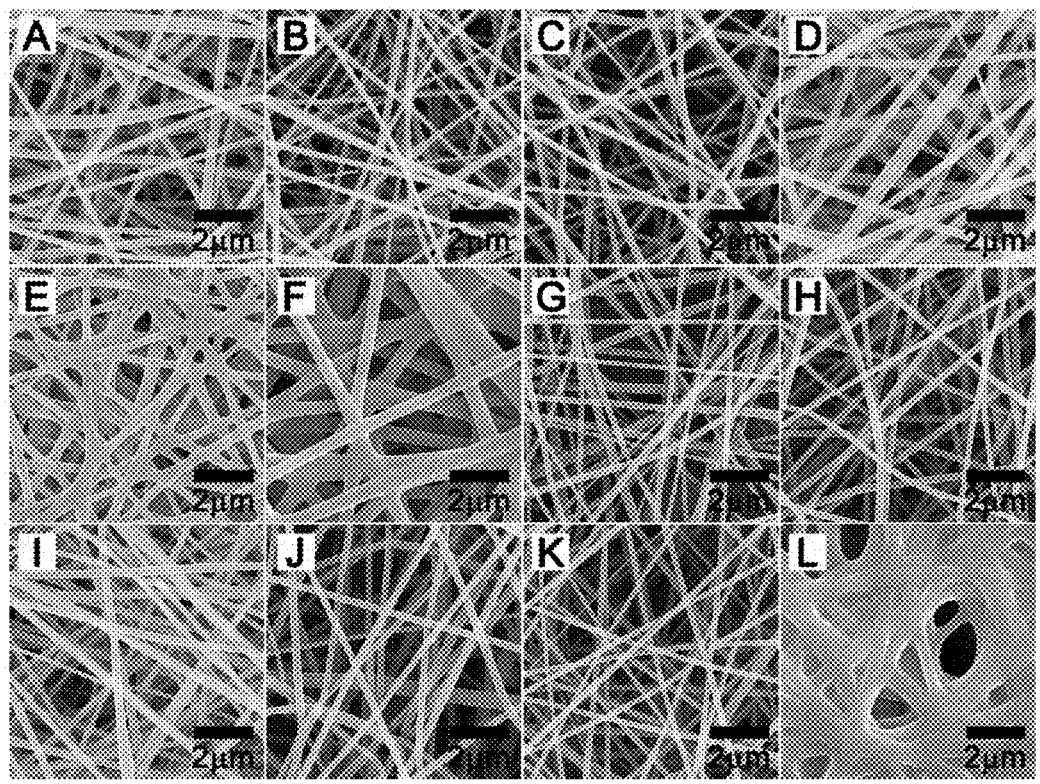
FIG. 1 shows scanning electron micrographs of electrospinning masks doped with different functional components, wherein A of FIG. 1 to L of FIG. 1 are the electrospinning masks doped with the functional components S1 to S12 in Table 1.

Scanning electron micrographs of the electrospinning masks doped with different functional components are shown as FIG. 1. It can be seen from FIG. 1 that the masks which were prepared by the electrospinning solutions with different functional components are nanofiber membranes composed of uniform nanofibers, and thus the solid masks have extremely high specific surface area capable of absorbing water fast and becoming invisible. It should be understood that the term invisible in the present invention means that after absorbing water, the solid mask would be dissolved rapidly and its initial solid form exists no more, and thereby even and smooth fibers are formed. The results of the scanning electron micrographs prove that uniform and smooth fibers were formed, without any functional substances leaking out from the fiber layer surface.

(2) Cellular Affinity Test

Cell planking: human normal skin fibroblasts (HSF) and human immortalized keratinocytes (Hacat) were planked into a 96-well plate with concentrations of 6000 cells and 12000 cells respectively, and cultured for 24 hours for later use.

Sterilization of masks and preparation of samples: on a super clean bench, the front side and the rear side of a mask were subjected to UV for 30 minutes for sterilization. The sterilized mask was dissolved in a culture medium containing blood serum to the maximum concentration of 20 mg/mL, and diluted in sequence to obtain samples in concentrations of 20, 10, 5, 3, 1, 0.5, 0.3, 0.1 and 0.05 mg/mL.

Sample loading: culture solutions in the 96-well plates with HSF and Hacat cells cultured for 24 hours therein were taken and added to the culture medium containing different concentrations of samples (sample groups); meanwhile, a control group was established, that is, a group of cells and normal culture medium containing blood serum; and a background deduction group was established, that is, a group of culture medium without planking cells, for deducting interference of the culture plate. Each group was provided with five parallel wells, and 100 μL of sample was added to each well.

Determination of cellular proliferation rate: after loading the samples, the culture mediums were cultured in the incubator for 24 hours, and then taken out for determination of cellular proliferation rate by the SRB (Sulforhodamine B) method.

Figure 2:
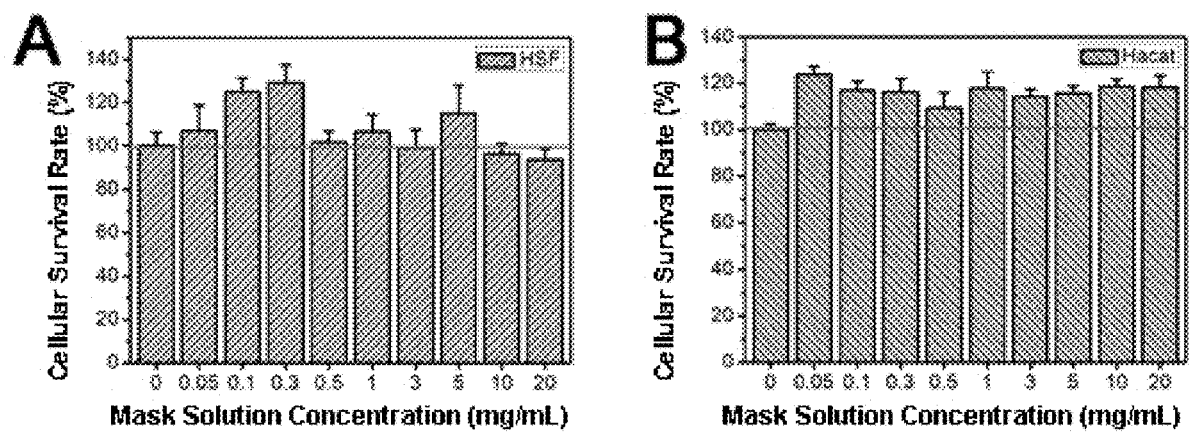
FIG. 2 shows the effects of a solution of solid mask S1 of different concentrations on proliferation rates of human normal skin fibroblasts (A of FIG. 2) and human immortalized keratinocytes (B of FIG. 2).

Determination results are shown in FIG. 2. FIG. 2 indicates that the mask solutions of different concentrations had no impact on the proliferation of the HSF and Hacat cells, and to some extent accelerated the growth of cells, indicating a very good cellular affinity. With the concentration increasing, cellular activity was enhanced. However, if the concentration of the electrospinning mask solution was further increased, the culture solution got thick which had impact on the growth of cells, thereby cell viability dropped to some extent. Results of IR and XRD can prove a relatively good compatibility of the functional substances and gelatin.

(3) Hen's Egg Test on the Chorioallantoic Membrane (HET-CAM)

Referring to Cosmetic Ocular Irritant and Corrosive HET-CAM Test Standard issued by the Entry-Exit Inspection and Quarantine Industry Standards, the solid mask of the present invention was first in solid state but dissolved fast when in contact with water, and thus an irritant grading method for transparent liquid subject and a terminal point grading method for solid such as particles and paste and turbid liquid subject are used to evaluate the irritation and corrosiveness of the electrospinning solid mask.

Irritant grading method: 0.3 mL of 20 mg/mL solid mask solution was added to the surface of a chorioallantoic membrane (CAM), the time of starting hemorrhage, blood vessel lysis and coagulation within 5 minutes was recorded, and six parallel tests were carried out.

Terminal point grading method: 30 mg of solid mask was directly applied to the CAM, and after 3 minutes, the residual mask was slightly washed off the CAM with normal saline, and condition of the CAM was observed and graded. Six parallel tests were carried out.

After in contact with the 20 mg/mL solid mask solution for 5 minutes, no substantial change was found in the CAM, and result of the irritant grading was non-irritant; after 30 mg of the electrospinning invisible mask was directly in contact with the CAM for 3 minutes, the residual mask was slightly washed off the CAM with normal saline, no hemorrhage, blood vessel lysis or coagulation occurred on the CAM subjected to contact with the dry mask, and thus the terminal point grading was 0 indicating that the mask was evaluated as non-irritant. The results all prove that the solid mask has good biocompatibility.

(4) Anti-Oxidation Test

Cell planking: HSF and Hacat cells were planked into a 96-well plate with concentrations of 6000 cells and 12000 cells respectively, and cultured for 24 hours for later use.

Sterilization and preparation of hydrogen peroxide solution and mask samples: on a super clean bench, hydrogen peroxide was dissolved in a culture solution to prepare a solution in concentration of 600 μmon, and the solution was subjected to filtration and sterilization with a 0.22 μm filter for later use. The front side and the rear side of mask S1 were subjected to UV for 30 minutes for sterilization. The sterilized mask was dissolved in the culture solution containing $H_2O_2$ to prepare a 1 mg/mL sample for later use.

Sample loading: culture solutions in the 96-well plates with HSF and Hacat cells cultured for 24 hours therein were taken and added to the culture solution containing 600 μmon $H_2O_2$ ($H_2O_2$ group) and the culture solution containing 600 μmon $H_2O_2$ and 1 mg/mL mask S1 ($H_2O_2$+ mask group) in sequence; as the above mentioned, a control group was established at the same time, that is, a group of cells and normal culture solution; and a background deduction group was established, that is, a group of culture solution without planking cells, for deducting interference of the culture plate. Each group was provided with five parallel wells, and 100 μL of sample was added to each well.

Determination of cellular proliferation rate: after loading the samples, the culture mediums were cultured in the incubator for 24 hours, and then taken out for determination of cellular proliferation rate by the SRB method.

Figure 3:
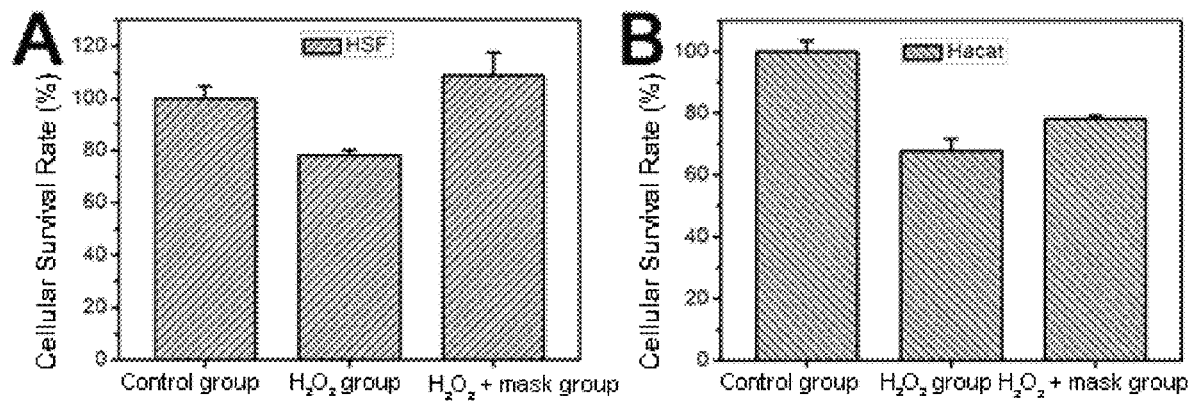
FIG. 3 shows the anti-oxidation performance of the solid mask S1 on the human normal skin fibroblasts (A of FIG. 3) and the human immortalized keratinocytes (B of FIG. 3).

HSF and Hacat cells show significantly decreased survival rates after adding hydrogen peroxide to the culture solutions of human normal skin fibroblasts and human immortalized keratinocytes, proving that modeling of hydrogen peroxide damage model is succeeded. When $H_2O_2$ and the electrospinning invisible mask were added simultaneously to the cellular culture solution, damage to the cell caused by hydrogen peroxide was repaired by the mask, especially the HSF cell of which activity would not be affected by hydrogen peroxide after adding the mask, wherein the cellular survival rate was even above 100% (shown in FIG. 3). It is proved that the electrospinning invisible mask containing carnosine has anti-oxidation performance and activity of skin care, which is capable of repairing the damaged cell membrane.

(5) Transdermal Test

Preparation of rat skin in vitro: abdomen skin of rat was taken, followed by removing the subcutaneous adipose tissue and connective tissue, and washed repeatedly with normal saline until there's no turbidity, for later use.

Preparation of sample: in the first group, the same amount of raw materials as the mask S1 were dissolved in water to prepare a 20 mg/mL raw material solution; and in the second group, 20 mg of the solid mask S1 was provided.

Transdermal test: rat skin was fixed on a diffusion cell of a transdermal test instrument, with the stratum corneum facing upward and the dermis facing an accepting cell. As for the first group, 1 mL of raw material solution was dropwise added to the rat skin; as for the second group, 1 mL of water was dropwise added to the skin first, and 20 mg of the solid mask S1 was applied to the wet rat skin; and then a liquid-feeding cell of each group was sealed with preservative film.

Sample taking and determination: when the transdermal test lasted for 15 minutes, 30 minutes, 1 hour, 2 hours, 4 hours, 6 hours, 8 hours, 12 hours and 24 hours, 0.5 mL of receptor fluid was extracted by a sampling needle respectively and the same amount of fresh receptor fluid was replenished. Transdermal amount of the functional substance was characterized indirectly by determining protein content in the extracted receptor liquid by the BCA method.

Determination method of retention amount of protein: after the transdermal test lasted for 24 hours, the rat skin was removed from the transdermal test instrument, and an effective area of the rat skin was cut off and washed clean with distilled water. After being drained off, the rat skin was cut into pieces with a scissor and placed in a 2 mL centrifuge tube, followed by adding 1 mL of ultrapure water, then subjected to homogenate for 3 minutes to 5 minutes via a homogenizer until there's no visible solid rat skin. After centrifugation, supernatant was filtered by a 0.22 μm filter membrane, and then retention amount of the functional substance in the rat skin was characterized indirectly by determining protein content in the supernatant by the BCA method.

Indirect results are shown in FIG. 4, wherein a represents the first group, and b represents the second group. It can be seen from FIG. 4 that when the transdermal test lasted for 15 minutes, 30 minutes, 1 hour, 2 hours, 4 hours, 6 hours, 8 hours, 12 hours and 24 hours, a total cumulative penetration amount of protein through the rat skin of the second group was far more than that of the first group, accounting for 130% to 160% of the first group. The total cumulative penetration amount of protein through the rat skin of the second group can reach up to approximately 1.8 mg. Also, the retention amount of protein in the rat skin of the second group was far less than that of the first group, and the retention amount of protein in the rat skin of the second group was about 0.6 mg merely. It can be proved from the experimental results that compared with the essence serum, the solid nanofiber mask in the present invention prepared by the electrospinning technology is easier to penetrate the stratum corneum and reach to the deep of the skin, which can improve the utilization rate of the functional substance.

Example 2

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 30 parts of gelatin, 1 part of soya bean lecithin and 0.1 part of functional substance shown as S1 in Table 1.

The preparation method includes the following steps:

step 1, preparation of electrospinning solution: using 50% (volume fraction) acetic acid solution as a solvent, adding gelatin, soya bean lecithin and a functional substance to the solvent, followed by mixing to form an even electrospinning solution;

step 2, electrostatic spinning: fixing the non-woven substrate layer to the roller, spinning the electrospinning solution of each group onto the hydrophobic substrate layer by an electrostatic spinning device to prepare and obtain solid masks, with a working voltage of 28 kV, a feeding velocity of 2 mL/hr, a spinning distance of 25 cm, and a relative humidity of working environment of 50%.

After a period of electrostatic spinning, the spun hydrophobic substrate layer was removed from the roller and cut by a mask cutter, and then the mask was folded into a quarter size and sealed in an aluminum foil packing bag for later use.

The nanofiber layer prepared had a fiber diameter ranging from 80 nm to 800 nm, and a fiber layer thickness of 0.05 mm to 2 mm.

Example 3

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 10 parts of gelatin, 30 parts of soya bean lecithin and 10 parts of functional substance shown as S1 in Table 1.

The preparation method includes the following steps:

step 1, preparation of electrospinning solution: using 90% (volume fraction) acetic acid solution as a solvent, adding gelatin, soya bean lecithin and a functional substance to the solvent, followed by mixing to form an even electrospinning solution;

step 2, electrostatic spinning: fixing the non-woven substrate layer to the roller, spinning the electrospinning solution of each group onto the hydrophobic substrate layer by an electrostatic spinning device to prepare and obtain solid masks, with a working voltage of 10 kV, a feeding velocity of 0.1 mL/hr, a spinning distance of 6 cm, and a relative humidity of working environment of 30%.

After a period of electrostatic spinning, the spun hydrophobic substrate layer was removed from the roller and cut by a mask cutter, and then the mask was folded into a quarter size and sealed in an aluminum foil packing bag for later use.

The nanofiber layer prepared had a fiber diameter ranging from 80-800 nm, and a fiber layer thickness of 0.05 mm to 2 mm.

Example 4

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 18 parts of gelatin, 15 parts of soya bean lecithin and 7.5 parts of functional substance shown as S1 in Table 1.

The preparation method includes the following steps:

step 1, preparation of electrospinning solution: using 90% (volume fraction) acetic acid solution as a solvent, adding gelatin, soya bean lecithin and a functional substance to the solvent, followed by mixing to form an even electrospinning solution;

step 2, electrostatic spinning: fixing the non-woven substrate layer to the roller, spinning the electrospinning solution of each group onto the hydrophobic substrate layer by an electrostatic spinning device to prepare and obtain solid masks, with a working voltage of 15 kV, a feeding velocity of 0.4 mL/hr, a spinning distance of 10 cm, and a relative humidity of working environment of 35%.

After a period of electrostatic spinning, the spun hydrophobic substrate layer was removed from the roller and cut by a mask cutter, and then the mask was folded into a quarter size and sealed in an aluminum foil packing bag for later use.

The nanofiber layer prepared had a fiber diameter ranging from 80 nm to 800 nm, and a fiber layer thickness of 0.05 mm to 2 mm.

Example 5

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 26 parts of gelatin, 2 parts of soya bean lecithin and 0.2 part of functional substance shown as S1 in Table 1.

The preparation method includes the following steps:

step 1, preparation of electrospinning solution: using 70% (volume fraction) acetic acid solution as a solvent, adding gelatin, soya bean lecithin and a functional substance to the solvent, followed by mixing to form an even electrospinning solution;

step 2, electrostatic spinning: fixing the non-woven substrate layer to the roller, spinning the electrospinning solution of each group onto the hydrophobic substrate layer by an electrostatic spinning device to prepare and obtain solid masks, with a working voltage of 23 kV, a feeding velocity of 1 mL/hr, a spinning distance of 18 cm, and a relative humidity of working environment of 45%.

After a period of electrostatic spinning, the spun hydrophobic substrate layer was removed from the roller and cut by a mask cutter, and then the mask was folded into a quarter size and sealed in an aluminum foil packing bag for later use.

The nanofiber layer prepared had a fiber diameter ranging from 80 nm to 800 nm, and a fiber layer thickness of 0.05 mm to 2 mm.

Comparative Example 1

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 29 parts of gelatin and 7.2 parts of functional substance shown as S1 in Table 1.

The preparation method was the same as that in Example 1.

The nanofiber layer prepared had a fiber diameter ranging from 80 nm to 800 nm, and a fiber layer thickness of 0.05 mm to 2 mm.

Comparative Example 2

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 29 parts of soya bean lecithin and 7.2 parts of functional substance shown as S1 in Table 1.

The preparation method was the same as that in Example 1.

The nanofiber layer prepared showed appearances of fractured yarns and holes, having a fiber diameter ranging from 80 nm to 800 nm, and a fiber layer thickness of 0.05 mm to 2 mm.

Comparative Example 3

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 8 parts of gelatin, 5 parts of soya bean lecithin and 7.2 parts of functional substance shown as S1 in Table 1.

The preparation method was the same as that in Example 1.

The nanofiber layer prepared showed appearances of fractured yarns and holes, having a fiber diameter ranging from 80 nm to 800 nm, and a fiber layer thickness of 0.05 mm to 2 mm.

Comparative Example 4

A solid mask, included a non-woven substrate layer and a nanofiber layer, wherein the nanofiber layer had a three-dimensional structure and was electro-spun onto the hydrophobic substrate layer through uniaxial electrostatic spinning technology, and the nanofiber layer was prepared by the following materials in parts by mass: 35 parts of gelatin, 5 parts of soya bean lecithin and 7.2 parts of functional substance shown as S1 in Table 1.

The preparation method was the same as that in Example 1.

The nanofiber layer prepared showed appearances of fractured yarns and holes, having a fiber diameter ranging from 80 nm to 800 nm, and a fiber layer thickness of 0.05 mm to 2 mm.

Test Results

Particularly, results of the transdermal test of Examples 2-5 and Comparative Examples 1-4 are shown in Table 2:

TABLE 2

Total cumulative penetration amount of protein (mg)

| Number | 15 min | 30 min | 1 hr | 2 hr | 4 hr | 6 hr | 8 hr | 12 hr | 24 hr |
|---|---|---|---|---|---|---|---|---|---|
| Example 2 | 0.23 | 0.27 | 0.31 | 0.45 | 0.7 | 0.77 | 0.9 | 1.1 | 1.4 |
| Example 3 | 0.24 | 0.28 | 0.32 | 0.47 | 0.72 | 0.78 | 0.92 | 1.12 | 1.45 |
| Example 4 | 0.27 | 0.31 | 0.39 | 0.54 | 0.83 | 0.94 | 1.14 | 1.25 | 1.69 |
| Example 5 | 0.26 | 0.29 | 0.37 | 0.49 | 0.78 | 0.86 | 1.05 | 1.21 | 1.57 |
| Comparative Example 1 | 0.23 | 0.26 | 0.3 | 0.45 | 0.68 | 0.76 | 0.86 | 1.02 | 1.35 |
| Comparative Example 2 | 0.22 | 0.24 | 0.28 | 0.42 | 0.63 | 0.7 | 0.82 | 0.96 | 1.32 |
| Comparative Example 3 | 0.19 | 0.21 | 0.26 | 0.34 | 0.5 | 0.66 | 0.74 | 0.97 | 1.15 |
| Comparative Example 4 | 0.17 | 0.18 | 0.24 | 0.28 | 0.42 | 0.56 | 0.62 | 0.81 | 1.12 |

TABLE 3

Total retention amount of protein in the skin

| Number | Total retention amount of protein in the skin/mg |
|---|---|
| Example 2 | 0.79 |
| Example 3 | 0.78 |
| Example 4 | 0.65 |
| Example 5 | 0.67 |
| Comparative Example 1 | 0.8 |
| Comparative Example 2 | 0.82 |
| Comparative Example 3 | 0.86 |
| Comparative Example 4 | 0.89 |

It can be seen from Table 2 and Table 3 that only when the material proportions and electrospinning parameters are in the optimized range, a nanofiber layer having high specific surface area and formed by nanofibers of even size may be obtained. In addition, within such range, nanoparticles and liposomes may be self-assembled which are conducive to transdermal absorption of the functional substances. If the formed nanofibers were agglomerated into clusters or dots, or had fractured yarns or holes, structure of the nanofiber layer would be severely affected; and too much or too less lecithin would go against the self-assembly, thereby, on the contrary, blocking pores and decreasing the transdermal absorption rate of functional substance.

Obviously, the above-mentioned embodiments of the invention are merely examples for clearly illustrating the invention, but are not intended to limit the implementations of the invention. For those of ordinary skills in the art, other different forms of changes or variations can be made on the basis of the above description. It is not necessary or possible to exhaust all the embodiments here. Any change, equivalent substitution, and improvement made within the spirit and principle of the invention shall fall within the protection scope of the claims of the invention.

What is claimed is:

1. A solid mask, comprising a hydrophobic substrate layer and a nanofiber layer, the nanofiber layer has a three-dimensional structure and is electro-spun onto the hydrophobic substrate layer through uniaxial electrostatic spinning technology, and the nanofiber layer is prepared by the following food-grade raw materials in parts by mass: 10 to 30 parts of gelatin, 1 to 30 parts of soya bean lecithin and 0.1 to 10 parts of a functional substance.

2. The solid mask according to claim 1, wherein the nanofiber layer is prepared by the following food-grade raw materials in parts by mass: 18 to 26 parts of gelatin, 2 to 15 parts of soya bean lecithin and 0.2 to 7.5 parts of the functional substance.

3. The solid mask according to claim 2, wherein the nanofiber layer is prepared by the following food-grade raw materials in parts by mass: 24 parts of gelatin, 5 parts of soya bean lecithin and 7.2 parts of the functional substance.

4. The solid mask according to claim 1, wherein the functional substance comprises one or more of white tremella polysaccharide, *Saussurea* polysaccharide, *Dendrobium officinals* Kimura et Migo, sodium hyaluronate, glycerin, nicotinamide, collagen peptide powder, collagen tripeptide, carnosine and hydrolyzed collagen.

5. The solid mask according to claim 4, wherein the functional substance is a mixture of hydrolyzed collagen, collagen peptide powder, collagen tripeptide and carnosine, wherein a mass ratio of hydrolyzed collagen to collagen peptide powder to collagen tripeptide to carnosine is 1:5:1:0.2.

6. The solid mask according to claim 5, wherein the collagen peptide powder has an average molecular weight of 2000 Dalton, and the collagen tripeptide has an average molecular weight of 280 Dalton.

7. The solid mask according to claim 1, wherein nanofibers of the nanofiber layer have a diameter of 80 nm to 800 nm, and the nanofiber layer has a thickness of 0.05 mm to 2 mm.

8. The solid mask according to claim 2, wherein the functional substance comprises one or more of white tremella polysaccharide, *Saussurea* polysaccharide, *Dendrobium officinale* Kimura et Migo, sodium hyaluronate, glycerin, nicotinamide, collagen peptide powder, collagen tripeptide, carnosine and hydrolyzed collagen.

9. The solid mask according to claim 8, wherein the functional substance is a mixture of hydrolyzed collagen, collagen peptide powder, collagen tripeptide and carnosine, wherein a mass ratio of hydrolyzed collagen to collagen peptide powder to collagen tripeptide to carnosine is 1:5:1:0.2.

10. The solid mask according to claim 9, wherein the collagen peptide powder has an average molecular weight of 2000 Dalton, and the collagen tripeptide has an average molecular weight of 280 Dalton.

11. The solid mask according to claim 3, wherein the functional substance comprises one or more of white tremella polysaccharide, *Saussurea* polysaccharide, *Dendrobium officinale* Kimura et Migo, sodium hyaluronate, glycerin, nicotinamide, collagen peptide powder, collagen tripeptide, carnosine and hydrolyzed collagen.

12. The solid mask according to claim 11, wherein the functional substance is a mixture of hydrolyzed collagen, collagen peptide powder, collagen tripeptide and carnosine, wherein a mass ratio of hydrolyzed collagen to collagen peptide powder to collagen tripeptide to carnosine is 1:5:1:0.2.

13. The solid mask according to claim 12, wherein the collagen peptide powder has an average molecular weight of 2000 Dalton, and the collagen tripeptide has an average molecular weight of 280 Dalton.

14. A preparation method for the solid mask according to claim 1, the preparation method comprises the following steps:
    step 1, preparation of electrospinning solution: adding gelatin, soya bean lecithin and the functional substance to a solvent, followed by mixing to form an even electrospinning solution;
    step 2, electrostatic spinning: spinning the electrospinning solution onto the hydrophobic substrate layer by an electrostatic spinning device to prepare and obtain the solid mask, with a working voltage of 10 kV to 28 kV, a feeding velocity of 0.1 mL/hr to 2 mL/hr, a spinning distance of 6 cm to 25 cm, and a relative humidity of working environment of 30% to 50%.

15. The preparation method for the solid mask according to claim 14, wherein in the step 2, the working voltage for the electrostatic spinning is 15 kV to 23 kV, the feeding velocity is 0.4 mL/hr to 1 mL/hr, the spinning distance is 10 cm to 18 cm, and the relative humidity of working environment is 35% to 45%.

16. The preparation method for the solid mask according to claim 14, wherein the solvent is 50% to 90% acetic acid solution.

* * * * *